United States Patent
Sekiguchi

(10) Patent No.: US 7,445,337 B2
(45) Date of Patent: Nov. 4, 2008

(54) OPHTHALMIC IMAGE SENSING APPARATUS

(75) Inventor: Kyoji Sekiguchi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 168 days.

(21) Appl. No.: 11/238,413

(22) Filed: Sep. 28, 2005

(65) Prior Publication Data

US 2006/0077343 A1 Apr. 13, 2006

(30) Foreign Application Priority Data

Sep. 29, 2004 (JP) ............................. 2004-283469

(51) Int. Cl.
*A61B 3/14* (2006.01)
(52) U.S. Cl. ..................... 351/207; 351/206; 351/205
(58) Field of Classification Search ................ 351/210, 351/212, 246, 206, 205, 207
See application file for complete search history.

(56) References Cited

U.S. PATENT DOCUMENTS

| | | | | |
|---|---|---|---|---|
| 4,200,362 A | * | 4/1980 | Pomerantzeff | ............... 351/221 |
| 4,257,688 A | * | 3/1981 | Matsumura | .................. 351/210 |
| 5,204,705 A | * | 4/1993 | Akiyama et al. | ............. 351/221 |
| 2004/0212780 A1 | * | 10/2004 | Itoh | ........................... 351/205 |

FOREIGN PATENT DOCUMENTS

JP 3-225387 10/1991

* cited by examiner

*Primary Examiner*—Ricky Mack
*Assistant Examiner*—James R Greece
(74) *Attorney, Agent, or Firm*—Morgan & Finnegan, L.L.P.

(57) ABSTRACT

An area having a diameter in which a peripheral area of an eye fundus image is covered with a mask is displayed on a monitor. When a region which may be abnormal is found in the vicinity of a boundary between the mask and the eye fundus image during image viewing, the display area enlarging means is operated. Then, an aperture area of the mask is enlarged to expand a display area of the eye fundus image, so the eye fundus image including some flare is displayed on a wide area. Therefore, an abnormal state of the region can be recognized.

5 Claims, 10 Drawing Sheets

OPHTHALMIC IMAGE SENSING APPARATUS

BACKGROUND OF THE INVENTION

1. Field of the Invention

The present invention relates to an ophthalmic image sensing apparatus for displaying an eye fundus image sensed by an eye fundus camera which is used in an ophthalmologic office or the like.

2. Related Background Art

In a conventional eye fundus camera (disclosed in Japanese Patent Application Laid-open No. H09-20627), in order to remove flare caused around an eye fundus image to make an effective image sensing area clear, an aperture mask serving as a light shielding member for shielding light traveling to a peripheral area is disposed immediately in front of an image sensing sensor to perform image sensing.

FIG. 12 illustrates an aperture mask image m, in which ma denotes a light shield area and mb denotes an aperture area. FIG. 13 is an optical structural view showing an image sensing unit. A changing mirror 2 and an image sensing lens 3 are disposed in front of an image sensing sensor 1. An aperture mask 4 is bonded to an imaging plane of the image sensing sensor 1.

In an optical system in which a filter, a cover glass, or the like is disposed immediately in front of the image sensing sensor 1, the aperture mask 4 cannot be located on the imaging plane of the image sensing sensor 1. Therefore, a separate re-imaging optical system is disposed and the aperture mask 4 is located therein.

The eye fundus image and the aperture mask image m which are optically sensed by such a structure are integrated into a single image. In the time of image viewing, the single image is displayed for diagnosis. In the proposal of the invention disclosed in Japanese Patent Application Laid-open No. H09-20627, an image sensed using the eye fundus camera provided without the above-mentioned aperture mask and the aperture mask image are electrically superimposed on each other to display the image into which the aperture mask image and the eye fundus image are integrated as in the conventional example.

SUMMARY OF THE INVENTION

However, in the conventional example, the displayed eye fundus image is an image into which the eye fundus image and the aperture mask image are optically or electronically integrated. Therefore, it is impossible to observe an area beyond (outside) a boundary area between the aperture mask image and the eye fundus image, that is, an area in which the eye fundus image is covered with the aperture mask image.

The present invention has been made to solve the above-mentioned problem. An object of the present invention is to provide an ophthalmic image sensing apparatus capable of changing the aperture mask image to display eye fundus image data which is acquired at the time of image sensing and includes image data corresponding to the area beyond the boundary area between the aperture mask image and the eye fundus image when the boundary area may be abnormal at the time of viewing the eye fundus image.

In order to achieve the above-mentioned object, according to an aspect of the present invention, the ophthalmic image sensing apparatus includes the following structure.

That is, the ophthalmic image sensing apparatus includes: an eye fundus camera for sensing an eye fundus image and converting the sensed eye fundus image to eye fundus image data; area setting means for setting a predetermined area for displaying the eye fundus image data; display means for displaying the eye fundus image data based on the set predetermined area; and area changing means for changing the predetermined area set by the area setting means.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with.

DETAILED DESCRIPTION OF THE PREFERRED EMBODIMENTS

Preferred embodiments of the present invention will now be described in detail in accordance with the accompanying drawings.

Embodiment 1

Figure 1:
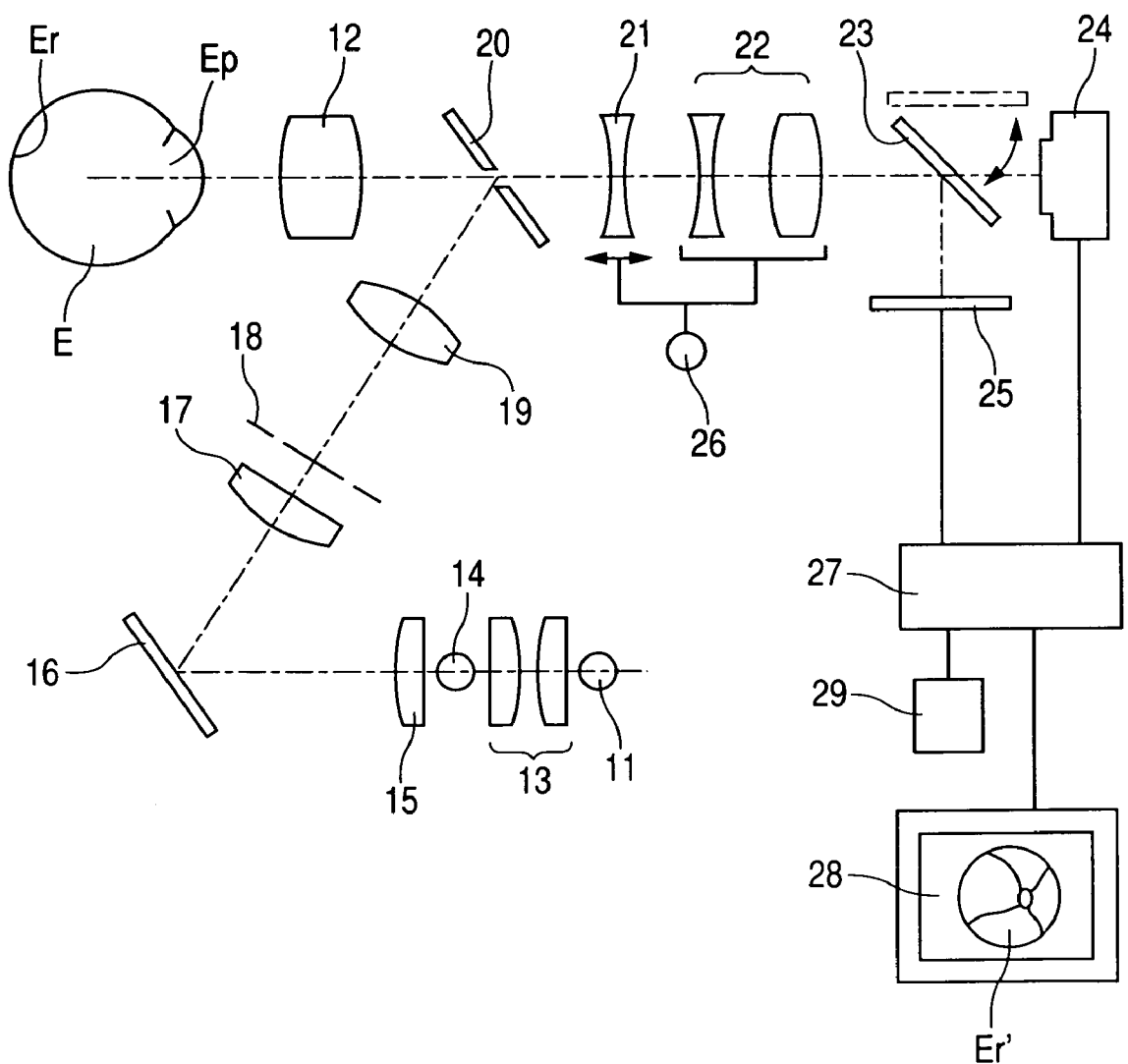
FIG. 1 is a structural diagram showing an ophthalmic image sensing apparatus according to Embodiment 1 of the present invention.

FIG. 1 is a structural diagram showing an ophthalmic image sensing apparatus according to this embodiment. A condenser lens 13, a still image sensing light source 14 such as a strobe scope light source, a condenser lens 15, a mirror 16, a lens 17, a diaphragm 18 having a ring aperture, a relay lens 19, and a holed mirror 20 having an aperture provided at a center portion thereof are disposed in order on an optical path from an examination alignment light source 11 to an objective lens 12. A focal lens 21, an image sensing lens 22 having an variable function, a changing mirror 23, an image pickup camera 24 having high resolution are disposed in order on an optical path located after the holed mirror 20. A high sensitive camera 25 for moving picture examination is disposed in a light reflecting direction of the changing mirror 23. The focal lens 21 and the image sensing lens 22 are moved in conjunction with a focal knob 26.

An output terminal of the image sensing camera 24 and an output terminal of the high sensitive camera 25 are connected with an image processing and displaying means 27. The output terminal of high sensitive camera 21 is also connected with a monitor 28 for displaying an eye fundus image Er' through image processing and displaying means 27. The image processing and displaying means 27 is also connected with a display area enlarging means 29 capable of changing an area displayed on the monitor 28 if necessary.

In such a structure, a light flux emitted from the examination alignment light source 11 passes through the condenser lens 13, the still image sensing light source 14, and the condenser lens 15 and reflected on the mirror 16 upward. The reflected light flux passes through the lens 17, the ring aperture of the diaphragm 18, and the relay lens 19 and reflected on the holed mirror 20 leftward. Then, the reflected light flux passes through the objective lens 12 to illuminate an eye fundus Er with the light flux through a pupil Ep of an eye to be examined E. The eye fundus image Er' produced by such illumination passes through the pupil Ep of the eye to be examined E, the objective lens 12, the focal lens 21, and the image sensing lens 22 and is reflected on the changing mirror 23 downward. The reflected eye fundus image Er' is formed on an image pickup plane of the high sensitive camera 25. The eye fundus image Er' is converted to an electrical signal and displayed on the monitor 28 through the image processing and displaying means 27.

A person who executes image sensing checks an image sensing position, an alignment state, and a focal state while observes the eye fundus image Er'. When the eye fundus is out of focus, the focal knob 26 is operated to move the focal lens 21 in an optical axis direction, thereby performing focusing.

After the completion of the focusing, when the person presses an image sensing switch which is not shown, the changing mirror 23 is removed from the optical path and flipped up to a position indicated by a broken line. In addition to this, the still image sensing light source 14 is turned on to emit light. A light flux emitted from the still image sensing light source 14 passes through the lens 15. After that, the light flux travels on the same optical path as that on which the light flux emitted from the examination alignment light source 11 travels, thereby illuminating the eye fundus Er. The eye fundus image Er' produced by such illumination passes through the pupil Ep, the objective lens 12, the aperture of the holed mirror 20, the focal lens 21, and the image sensing lens 22 and is formed on an image pickup plane of the image pickup camera 24.

The image picked up by the image pickup camera 24 is converted to an electrical signal. Then, the image is stored in an image memory of the image processing and displaying means 27 and displayed as a still image on the monitor 28.

Figure 2:
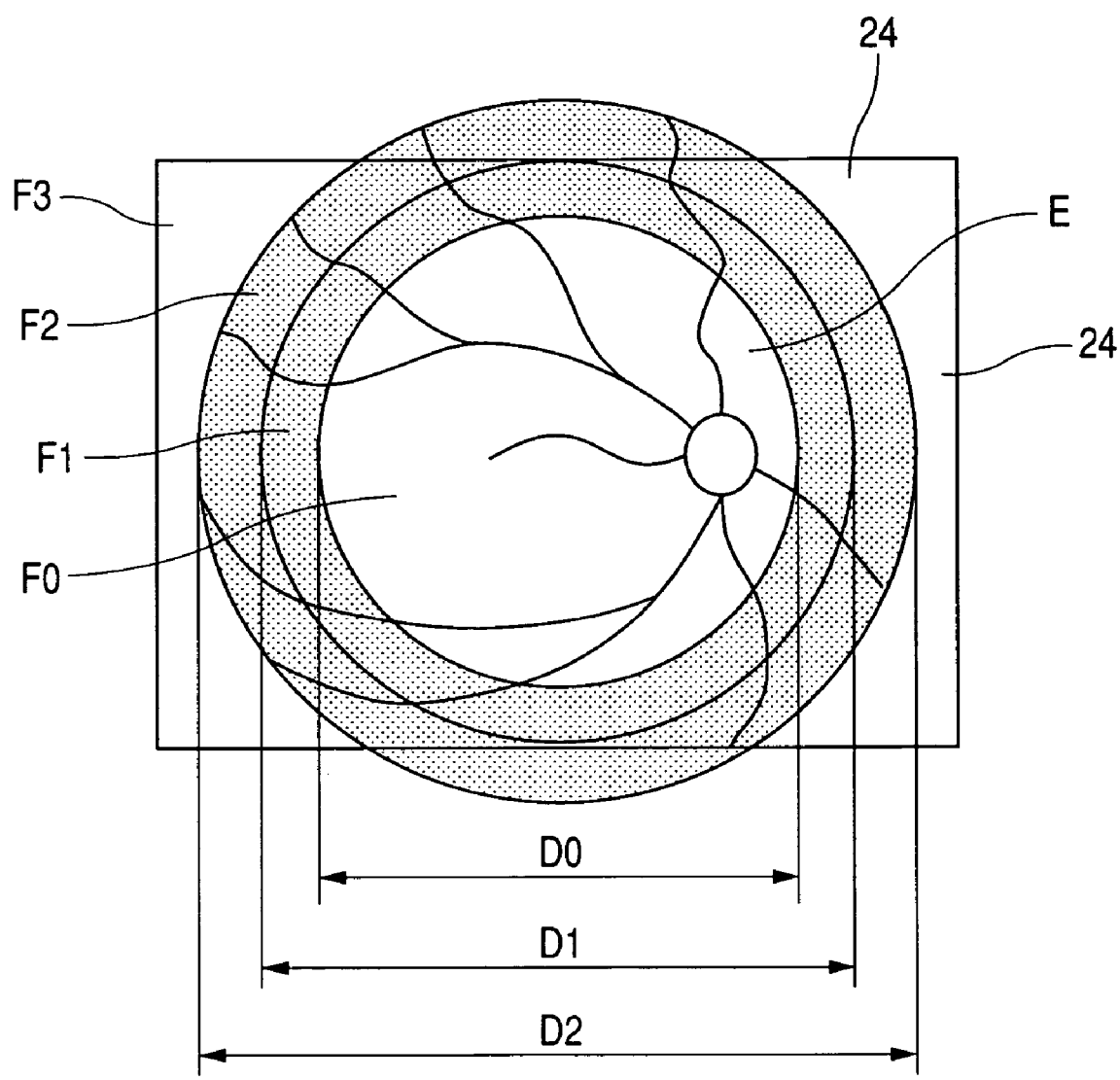
FIG. 2 is an explanatory view showing an eye fundus image on an image sensing camera.

FIG. 2 illustrates a positional relationship between the image picked up by the image pickup camera 24 and the image pickup camera 24. An examination optical system and the image pickup camera 24 are disposed such that the optical axis of examination optical system and the center of the image pickup camera 24 become substantially concentric. Therefore, the eye fundus image Er' is formed in substantially the center of the image pickup camera 24. The picked up image can be divided into areas F0 to F3. The area F0 (D0 in diameter) includes no flare and is effective in diagnosis. The area F1 (D1 in diameter) includes some flare but reflects the eye fundus image Er'. The area F2 (D2 in diameter) includes many flares and reflects, for example, an internal image of the eye fundus camera together with the blurred eye fundus image Er'. The area F3 is an ineffective area which is located outside the area F2 and in which the eye fundus image Er' is completely blurred.

Figure 3:
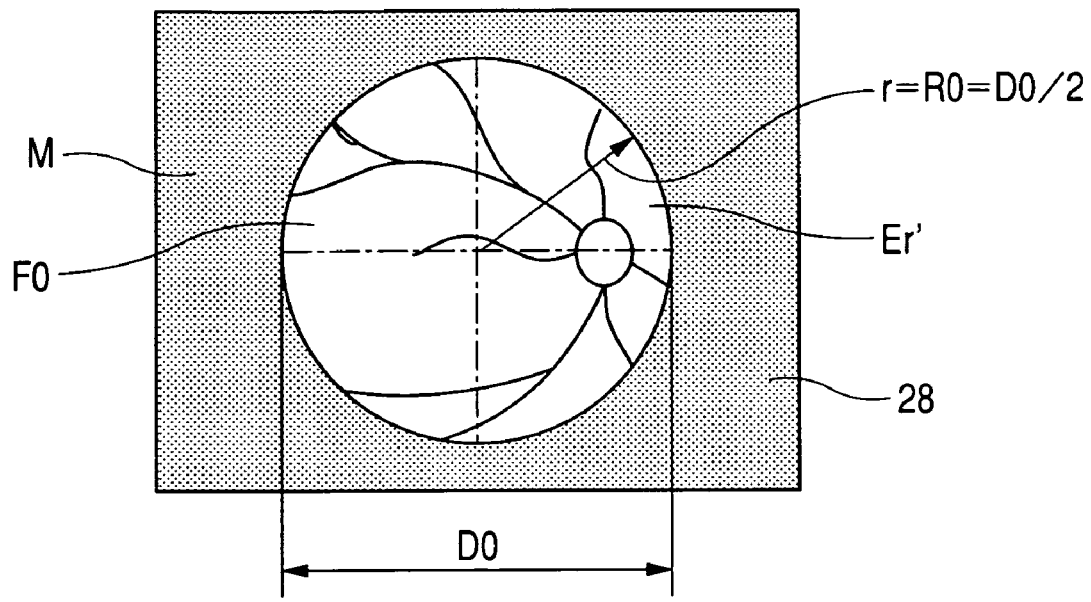
FIG. 3 is an explanatory view showing the eye fundus image on a monitor.

FIG. 3 is an explanatory view showing a still image of the eye fundus image Er' displayed on the monitor 28. In actual use, for example, operational buttons for operating patient information and image display applications are displayed on the monitor 28. In FIG. 3, only the eye fundus image Er' is shown. Only the area F0 having the diameter D0 is normally displayed.

Figure 4:
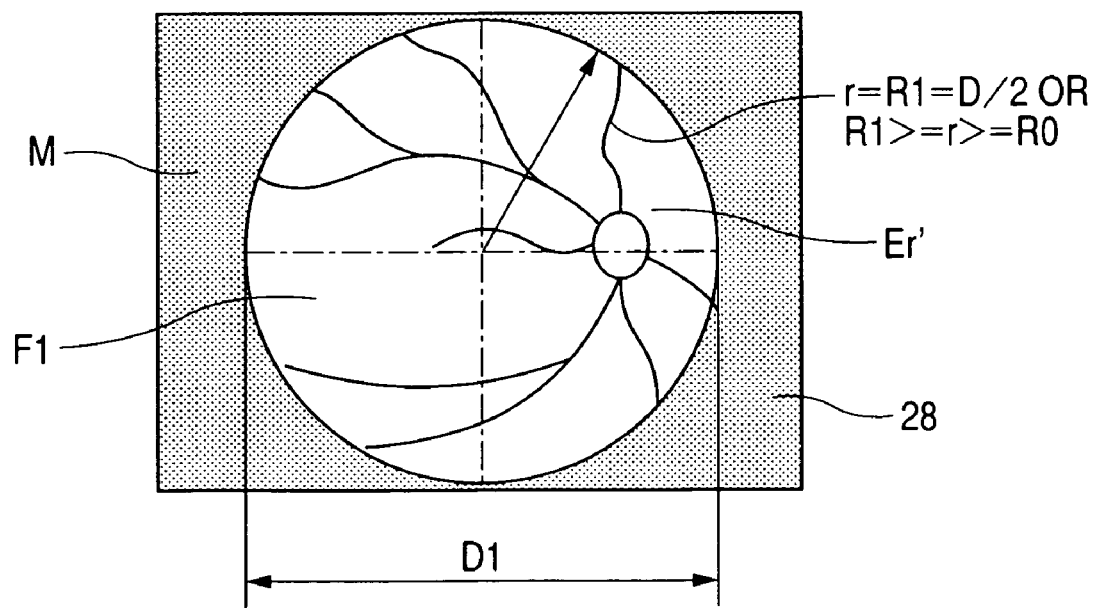
FIG. 4 is an explanatory view showing the eye fundus image on the monitor, which is subjected to area enlarging operation.

Assume that a peripheral area on which an image is not displayed is a mask M. When a region which may be abnormal is found in the vicinity of a boundary between the mask M and the eye fundus image Er' during image viewing, the display area enlarging means 29 is operated. Then, as shown in FIG. 4, an aperture area of the mask M is enlarged to expand a display area of the eye fundus image Er', so the picked up eye fundus image Er' including some flare is displayed. Therefore, it is possible to determine whether or not the region is really abnormal and thus another image sensing is necessary.

A boundary between the area F0 having the diameter D0 and the mask M is set with some margin, so the eye fundus image Er' can be recognized independent on a personal difference. However, an entering state of flare is changed in an area outside the boundary depending on a personal difference, image sensing conditions, and the like. Therefore, the percentage that the eye fundus image Er' can be recognized reduces.

The area F0 which flare does not enter can be determined in advance as an area having the diameter D0 (radius R0) from the center of a sensor based on an optical design. The area F0 is narrowed to the inside somewhat such that the personal difference of the eye to be examined E can be reduced. In a normal state, only the area F0 is displayed or printed out for diagnosis and explanation to a patient. When the flare enters the peripheral area, it is impossible to determine whether or not normal image sensing can be performed. In addition to this, an image diagnostic area is indefinite, so diagnostic efficiency reduces. Therefore, only a clear area is normally displayed.

With respect to the peripheral area, the diameter D1 (radius R1) and the diameter D2 (radius R2) are determined in advance for the area F1 and the area F2, respectively, based on the optical design and experiments on human eye image sensing and the like. It is important to set the radius R2 for determining an outer edge of the area F2. The area F2 reflects an image other than the eye fundus image Er', for example, an internal image of the eye fundus camera, so it is likely to miss the diagnosis. Therefore, the area F2 is an area in which display on the monitor 28 for diagnosis and printing are inhibited. Values such as the diameters (radius) are stored in the image memory of the image processing and displaying means 27.

When an image to be displayed on the monitor 28 is selected, a peripheral area outside a circle having the radius R0 from the center of the image is set as a transmission area. When the image to which the transmission area is set is displayed using a black background, only a central area (radius R0) of the image is visualized. That is, an area around the central area is displayed with a background color (black in this embodiment) on the monitor 28. Alternatively, an alpha channel may be added to an image to be displayed and a mask image to be displayed may be superimposed on the image.

When the display area is to be enlarged, as shown in FIG. 4, the display area enlarging means 29 may be operated to change a radius r of the image to be displayed to R1. The radius r may be changed in a range of R0 to R1 by the mouse operation or the like. An area which does not reflect the eye fundus image Er' is set as an upper limit area, so the internal image of the eye fundus camera is not displayed.

Figure 5:
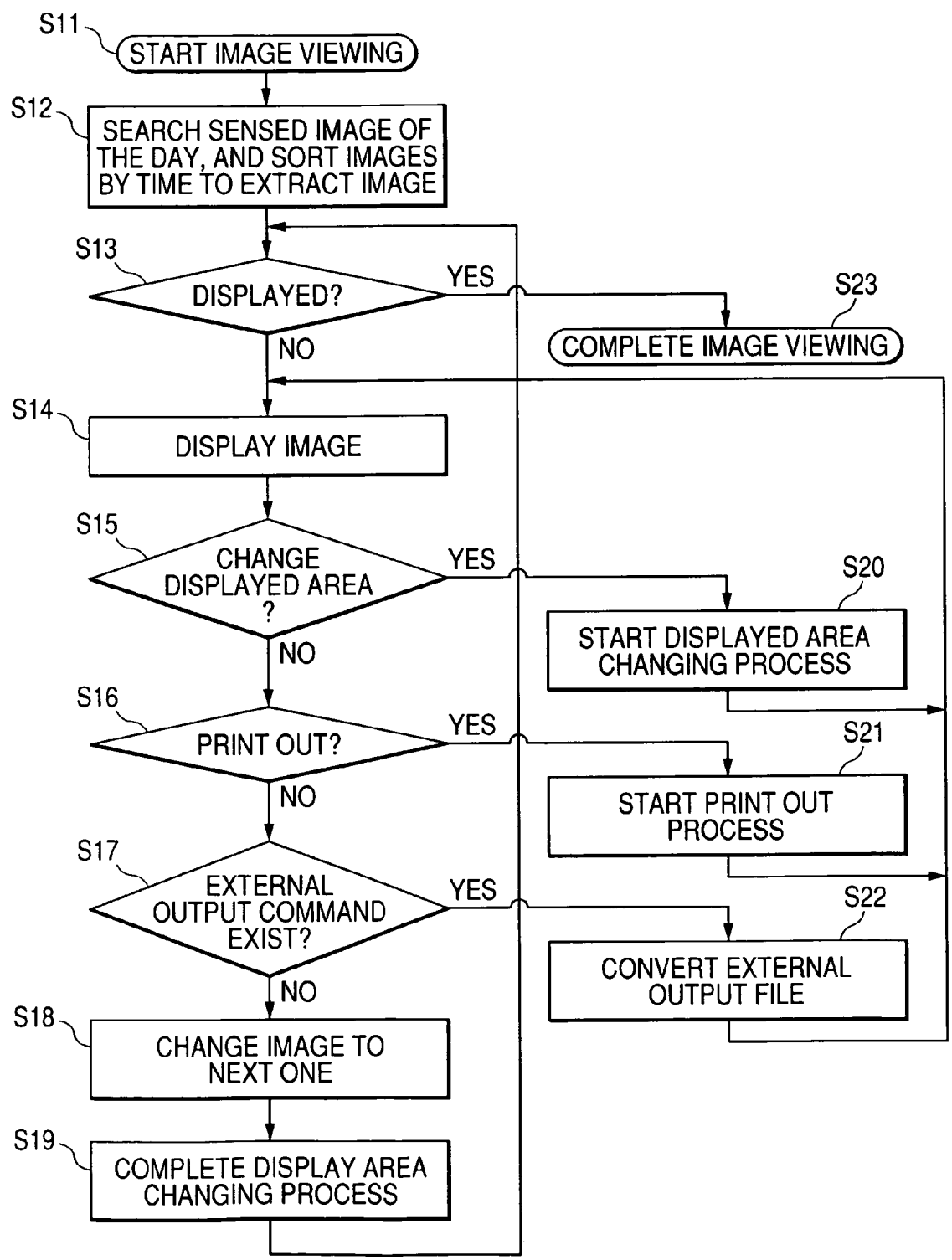
FIG. 5 is a processing flowchart.

FIG. 5 is a processing flowchart in the case where the sensed eye fundus image Er' is subjected to image viewing. In Step S11, the image viewing starts. First, in Step S12, an image sensed at the day is searched. Image sensing information is added to a file including the sensed image, so sorting is performed based on image sensing dates to extract the image. In Step S13, the completion of displayed images is checked. In Step S14, a first image is displayed. At this time, control is made so as to display the area F0.

In Steps S15 to S17, processing conditions are determined. In Step S15, whether or not an area to be displayed is enlarged is checked. In Step S16, whether or not the displayed image is printed out. In Step S17, whether or not the file is outputted to provide the displayed image to an outside. When a check result is NO in each of Steps S15 to S17, next image changing is performed in Step S18. In Step S19, a display area changing process is completed.

When the check result is NO in Step S15 and the display area changing process is not performed, processing returns to Step S13 without any processing. When the displayed area is to be changed in Step S15, processing goes to Step S20 to start the display area changing process. Then, in step S14, an actual display area, that is, the aperture area of the mask M is changed and displayed on the monitor 28. When a print out command is YES in Step S16, a print out process is performed in Step S21 to print out the image displayed in Step S14.

When an external output command is YES in Step S17, in Step S22, a visualized area which is currently displayed for external output and a background are superimposed on each other and the resultant information is format-converted to an image file. Processing control returns to Step S14 and whether or not a next process command exists is checked. When images are successively displayed based on the above-mentioned manner and the display of all images is completed, processing goes from Step S13 to Step S23 and the image viewing is completed.

Embodiment 2

Figure 6:
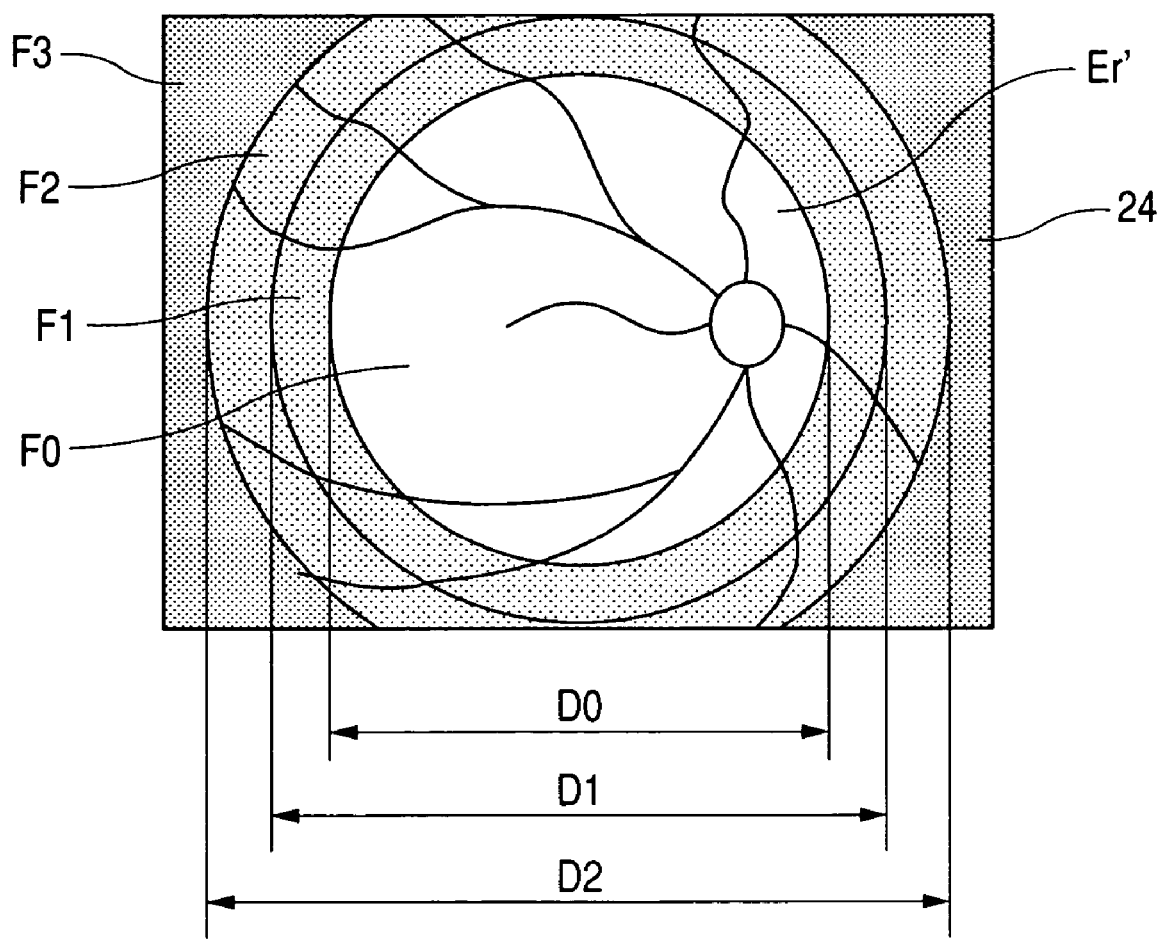
FIG. 6 is an explanatory view showing an eye fundus image on an image sensing camera in Embodiment 2.
Figure 7:
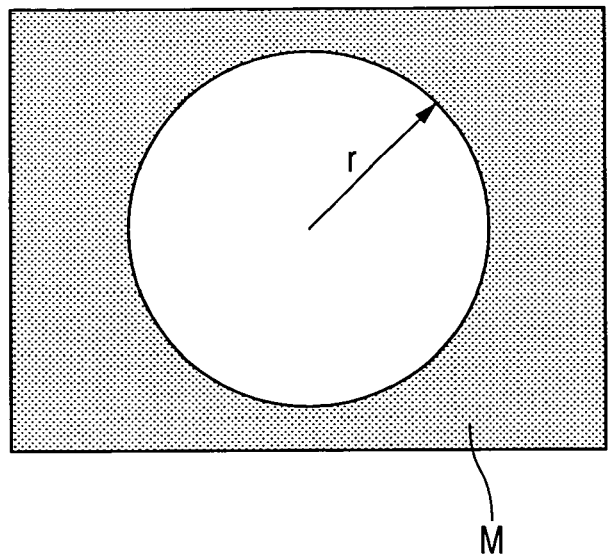
FIG. 7 is an explanatory view showing a mask.

FIG. 6 illustrates an original image of the eye fundus image Er' which is acquired at the time of eye fundus image sensing in Embodiment 2. FIG. 7 illustrates the mask M. The mask M has the radius r and is formed corresponding to a size of the original image by the image processing and displaying means 27. The control is made such that the radius r indicates the internal region of a circle. When the display area enlarging means 29 is operated, the radius r is changed to change the display area. Even in this case, the display area can be enlarged up to only the upper limit area.

Embodiment 3

Figure 8:
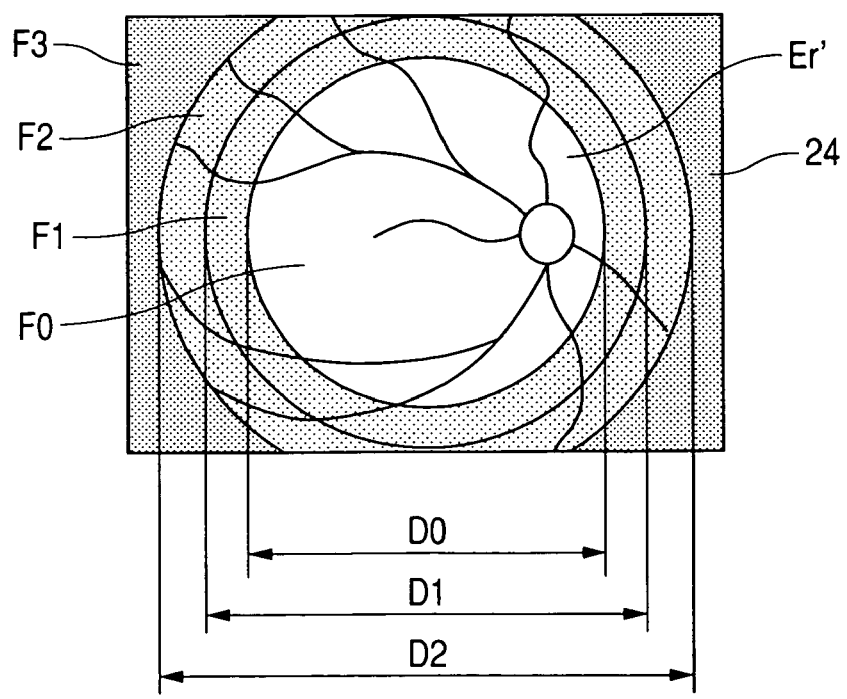
FIG. 8 is an explanatory view showing an eye fundus image on an image sensing camera in Embodiment 3.
Figure 9A:
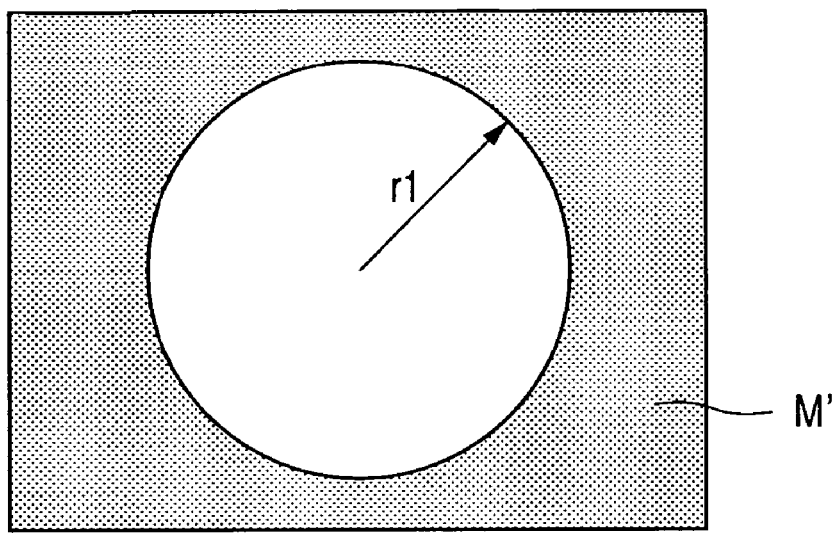
FIGS. 9A and 9B are explanatory views showing masks.
Figure 9B:
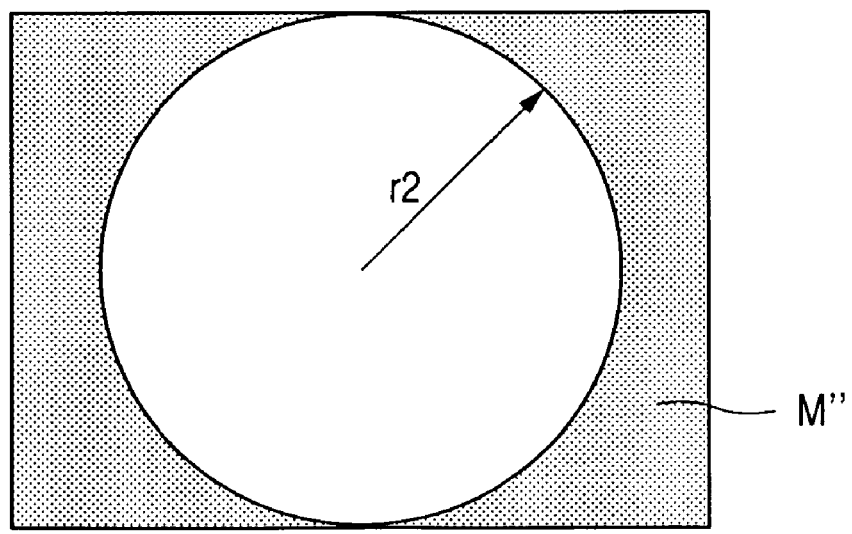

FIG. 8 illustrates an original image of the eye fundus image Er' which is acquired at the time of eye fundus image sensing in Embodiment 3. FIG. 9A illustrates a mask M' having a normal radius r1. FIG. 9B illustrates a mask M" having a radius r2 at the time of enlarging. Switching between two types of masks M' and M" is performed by the operation of the display area enlarging means 29. Therefore, an eye fundus image within a circle having the radius r1 or r2 from the image center is displayed.

Embodiment 4

Figure 10:
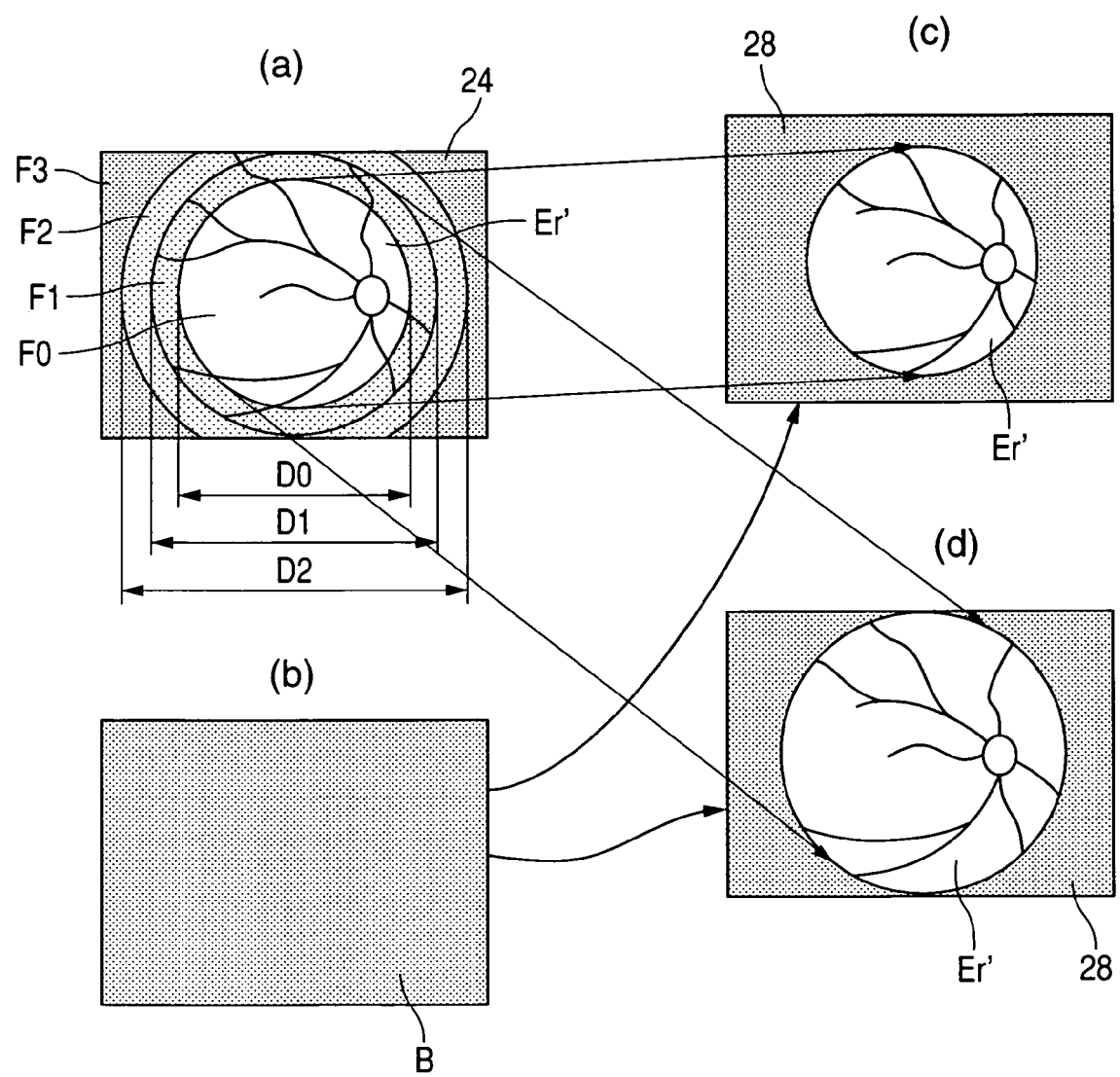
FIG. 10 is an explanatory view in the case where a predetermined area on an eye fundus image is copied and superimposed on a blank image.

FIG. 10 is an explanatory view in Embodiment 4. (a) of FIG. 10 illuminates an original image of the eye fundus image Er' which is acquired at the time of eye fundus image sensing and (b) of FIG. 10 illustrates a blank image B having the same size as that of the original image. (c) of FIG. 10 illustrates the eye fundus image Er' which is a normal display image and acquired by copying an image within a range of the radius r1 from the image center. As shown in (d) of FIG. 10, an eye fundus image is displayed by copying pixel values in the blank image B at the same coordinates. When the display area enlarging means 29 is operated, a size of a copying area of the eye fundus image Er' is changed to enlarge the display area.

Figure 11:
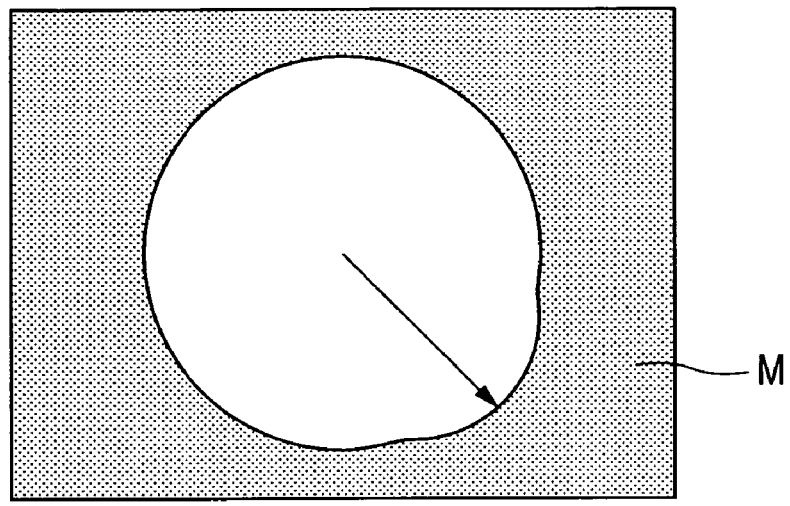
FIG. 11 is an explanatory view in the case where a part of a mask is enlarged.
Figure 12:
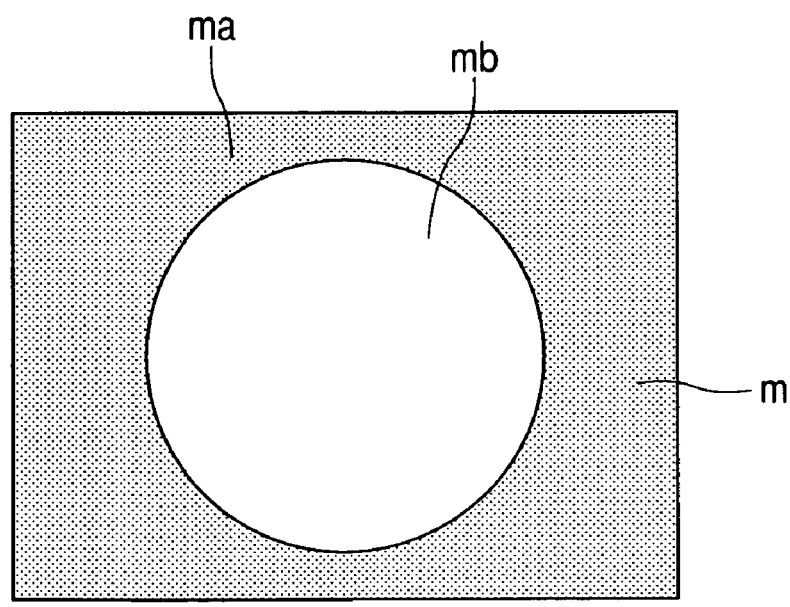
FIG. 12 is an explanatory view showing a conventional mask.
Figure 13:
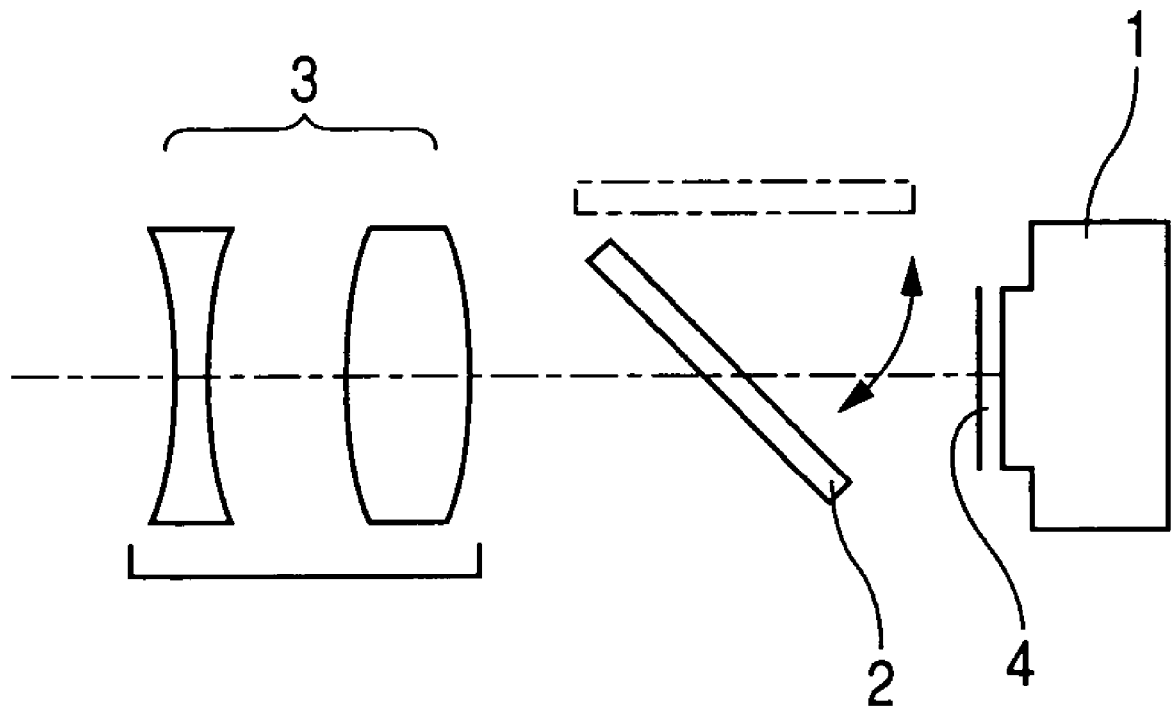
FIG. 13 is a structural view showing a conventional image sensing unit.

In the above description, the display area produced by the mask M is changed concentrically. As shown in FIG. 11, it is also possible to expand only a part of the display area produced by the mask M on a screen, which is dragged by a mouse. The display area produced by the mask M is not limited to an accurate circular shape and may be an elliptical shape.

According to the ophthalmic image sensing apparatus in any embodiment, in the case where the eye fundus data within the area set by the area setting means includes a region to be paid attention to, such as a lesion, even when the eye fundus data includes the flare, the area can be enlarged to display the eye fundus data. Therefore, the necessary number of re-image-sensing can be significantly reduced, so there is an effect of improving diagnostic efficiency. In addition, the percentage that re-image-sensing is required reduces, so there is an effect of reducing a medical cost and a burden on a patient's side.

As described above, according to the present invention, it is possible to provide the ophthalmic image sensing apparatus capable of changing the aperture mask image to display eye fundus image data which is acquired at the time of image sensing and includes image data corresponding to the area beyond the boundary area between the aperture mask image and the eye fundus image when the boundary area may be abnormal at the time of viewing the eye fundus image.

As many apparently widely different embodiments of the present invention can be made without departing from the spirit and scope thereof, it is to be understood that the invention is not limited to the specific embodiments thereof except as defined in the claims.

This application claims priority from Japanese Patent Application No. 2004-283469 filed Sep. 29, 2004, which is hereby incorporated by reference herein.

What is claimed is:

1. An ophthalmic image sensing apparatus, comprising:
   image sensing means for obtaining eye fundus image data by sensing a fundus of an eye to be to be examined;
   image processing means for superimposing mask image data which is used for shielding the eye fundus image data except for a visible area which is effective in diagnosis so as to initially shield flare light on the eye fundus image data;
   display means for displaying image data provided by the image processing means; and
   changing means for changing a shape of the visible area in the mask image data,
   wherein the visible area of the mask image data is initially a circular area, and the changing means changes the mask image data to make the visible area into an elliptical shape.

2. An ophthalmic image sensing apparatus according to claim 1, wherein the visible area of the mask image data is initially a circular area, and the changing means changes the mask image data by partially enlarging diameter of the circular area.

3. An ophthalmic image sensing apparatus according to claim 1, wherein the changing means comprises a plurality of mask image data each in which visible area is different from the other and selects one of the plurality of mask image data.

4. An ophthalmic image sensing method comprising the steps of:

sensing a fundus image data of a fundus of an eye to be examined, or selecting fundus image data which is stored;

superimposing a mask image data including a visible area and stored on the sensed or selected fundus image data;

displaying a superimposed image data; and changing the visible area of the mask image data from a circular area to an elliptical shape.

5. An ophthalmic image sensing apparatus according to claim 1, further comprising:

instruction means for providing an instruction to the display means so as to specify the eye fundus image data to be displayed on the display means, and wherein the changing means changes the mask image data to change the shape of the visible area on the basis of the instruction from the instruction means.

* * * * *